March 21, 1944. F. K. BAXTER Plant Pat. 619

APPLE TREE

Filed May 13, 1943

INVENTOR
Frederick K. Baxter
BY Thos. E. Scofield
ATTORNEY.

Patented Mar. 21, 1944

Plant Pat. 619

UNITED STATES PATENT OFFICE

619

APPLE TREE

Frederick K. Baxter, Nauvoo, Ill., assignor to Gem City Vineland Company, Nauvoo, Ill., a partnership composed of Frederick K. Baxter, Emil O. Baxter, and Cecil J. Baxter, Jr.

Application May 13, 1943, Serial No. 486,757

1 Claim. (Cl. 47—62)

This invention relates to a new and distinct variety of apple tree. The tree originated as a seedling of unknown parentage in the orchard of the Gem City Vineland Company, at Nauvoo, Illinois.

Grafts of the tree top-worked on other trees have since 1933 reproduced apples true to this type.

Figure 1:
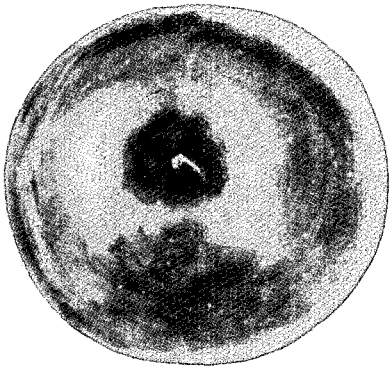
Figure 2:
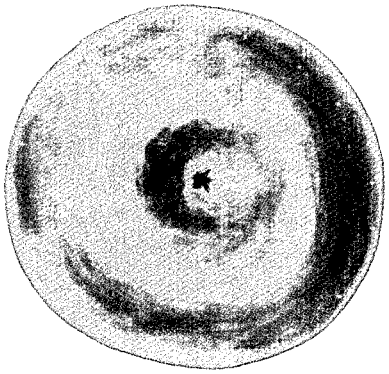
Figure 3:
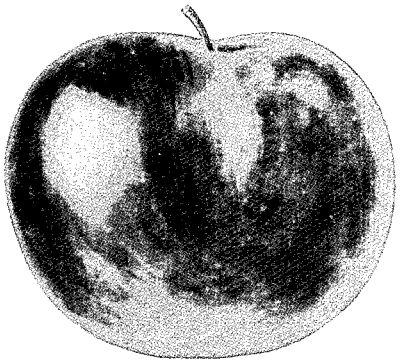
Figure 4:
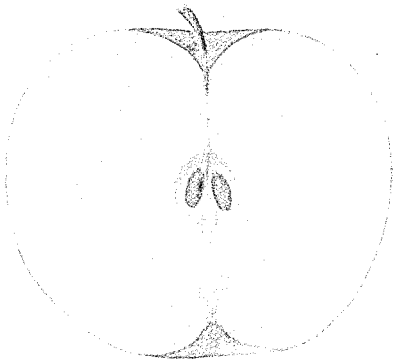

In the drawing, Figs. 1 and 2 show opposite end views, Fig. 3 a side elevation, and Fig. 4 a vertical section, of the ripe fruit of this variety.

The growth habits of the trees of this variety are somewhat the same as those of the Turley Winesap, with the fruit holding well to the tree considerably longer than the Turley or other Winesap variety. One salient and distinctive feature of this new variety is its hardiness to withstand sudden and severe winter cold. The trees are large besides being exceedingly hardy and vigorous, are spreading in character, branches stout, and spaced to form trees of the open head type, twigs are short to medium and regularly spaced. The trees bloom early along with the Red Delicious and Jonathan and the blossoms pink to red in color.

The trees are early bearers, the fruit being well spaced, usually 6 to 10 inches apart, bearing with uniformity throughout the tree. The fruit hangs well, is uniform, medium in size, heavy in weight, and in color is a crimson red, turning to a maroon or deep reddish black, with shading to a lighter red or russet yellow, usually around the calix. In shape the fruit is substantially round, or in some specimens slightly flattened at top and bottom. The skin is medium tough, has a smooth surface, glossy to waxy or almost oily to feel. The flesh is a whitish color with yellow tinge, firm, crisp and juicy. The date of ripening of the fruit is late October in west central Illinois. The fruit is an excellent shipper and winter keeper, holding in common storage until May or later.

Having thus described my invention, I claim:

A new and distinct variety of apple tree characterized by its early bloom, vigorous growth, stout branches, hardiness and ability to withstand sudden and severe winter cold and by a fruit which is early and regular bearing, maroon to black in color shading to russet yellow usually about the calyx, spherical to ellipsoidal in shape with the flattened portion at the stem and calyx, the skin medium tough and having a waxy appearance and feel, the meat yellowish to white, crisp, firm and juicy, and having excellent shipping and storage qualities substantially as shown and described.

FRED. K. BAXTER.